(12) United States Patent
Pruvot et al.

(10) Patent No.: US 7,993,274 B2
(45) Date of Patent: Aug. 9, 2011

(54) METHOD, SYSTEM, AND COMPUTER PRODUCT FOR AUTOMATICALLY EXTRACTING AND TRACKING CARDIAC CALCIFICATIONS AND DETERMINING A TRACKING CENTERLINE

(75) Inventors: Celine Pruvot, Buc (FR); Laurent Jean Lucien Stefani, Paris (FR)

(73) Assignee: General Electric Company, Schenectady, NY (US)

( * ) Notice: Subject to any disclaimer, the term of this patent is extended or adjusted under 35 U.S.C. 154(b) by 522 days.

(21) Appl. No.: 11/985,775

(22) Filed: Nov. 16, 2007

(65) Prior Publication Data

US 2008/0119734 A1 May 22, 2008

Related U.S. Application Data

(60) Provisional application No. 60/866,983, filed on Nov. 22, 2006.

(51) Int. Cl.
*A61B 8/14* (2006.01)
*G06K 9/00* (2006.01)

(52) U.S. Cl. ........................................ 600/467; 382/131

(58) Field of Classification Search .................. 600/407, 600/409, 437, 443, 466–467; 382/128, 131, 382/170–173
See application file for complete search history.

(56) References Cited

U.S. PATENT DOCUMENTS

| | | | |
|---|---|---|---|
| 6,148,095 A * | 11/2000 | Prause et al. | 382/131 |
| 6,251,072 B1 * | 6/2001 | Ladak et al. | 600/443 |
| 7,031,426 B2 | 4/2006 | Iatrou et al. | |
| 7,330,576 B2 * | 2/2008 | Raman et al. | 382/128 |
| 7,333,648 B2 * | 2/2008 | Edic et al. | 382/131 |
| 7,356,367 B2 | 4/2008 | Liang et al. | |
| 7,369,691 B2 * | 5/2008 | Kondo et al. | 382/128 |
| 7,397,935 B2 * | 7/2008 | Kimmel et al. | 382/128 |
| 7,480,398 B2 * | 1/2009 | Kleen et al. | 382/128 |
| 7,590,270 B2 | 9/2009 | Asbeck et al. | |
| 7,657,299 B2 | 2/2010 | Huizenga et al. | |
| 7,702,141 B2 * | 4/2010 | Sirohey et al. | 382/131 |
| 7,860,283 B2 * | 12/2010 | Begelman et al. | 382/128 |
| 2006/0036167 A1 * | 2/2006 | Shina | 600/433 |

* cited by examiner

*Primary Examiner* — Francis Jaworski
(74) *Attorney, Agent, or Firm* — Cantor Colburn LLP

(57) ABSTRACT

Systems, methods and computer products for automatically extracting automatically cardiac calcifications and obtaining a centerline in the tracking. Exemplary embodiments include a method of cardiac diagnostics, the method including obtaining coronary tree segmentation to obtain cardiac volume information, splitting the volume into portions to obtain an adjacency graph, computing a mean of a sub-volume of the volume, obtaining gray value segmentation of the sub-volume, defining a centerline of a blood vessel that avoids calcifications within the blood vessel and detecting an actual centerline of the blood vessel and enhancing lumen visualization of the blood vessel.

28 Claims, 9 Drawing Sheets

METHOD, SYSTEM, AND COMPUTER PRODUCT FOR AUTOMATICALLY EXTRACTING AND TRACKING CARDIAC CALCIFICATIONS AND DETERMINING A TRACKING CENTERLINE

Priority based on U.S. Provisional Patent Application, Ser. No. 60/866,983, filed Nov. 22, 2006, and entitled, "Method, System and Computer Product for Cardiac Calcification Tracking Display" is claimed, the content of the legally related application is incorporated herein by reference in its entirety.

BACKGROUND

The present disclosure generally relates to cardiac diagnostics, and more particularly, to systems methods and computer products for automatically extracting cardiac calcifications and obtaining a better centerline in the tracking.

Most cardiac diagnostics include vascular analysis and coronary stenosis analysis. The cardiac calcifications obstruct the visualization of the lumen of the coronaries. A display of the lumen without the calcifications helps the diagnosis (mode ON/OFF). A good lumen extraction and visualization would be possible if there exists perfect detection of the centerline (centerline in the lumen). However, current techniques tend to detect the centerline inside the cardiac calcifications instead of the actual center of the lumen. Therefore, the lumen visualization is upset and the stenosis measurement is not reliable if the user performs no edition of the lumen centerline or contours. Current methods also detect the centerline of the vessel and provide lumen and reformatted views to help the reading. The stenosis measurements (diameter, length) also depend on the reliability of lumen volume. In addition, a realistic display of the inside of the vessel helps the diagnosis.

SUMMARY

Disclosed herein is a method of cardiac diagnostics, the method including obtaining coronary tree segmentation to obtain cardiac volume information, splitting the volume into portions to obtain an adjacency graph, computing a mean of a sub-volume of the volume, obtaining gray value segmentation of the sub-volume, defining a centerline of a blood vessel that avoids calcifications within the blood vessel and detecting an actual centerline of the blood vessel and enhancing lumen visualization of the blood vessel.

Further disclosed herein is a method for extracting and tracking cardiac calcification image volumes in a blood vessel, the method including obtaining intravascular ultrasound views of the blood vessel, defining a blood vessel tree segmentation of the intravascular ultrasound views and extracting an image volume of cardiac calcifications from the tree segmentation.

Further disclosed herein is a system for extracting and tracking cardiac calcifications in a blood vessel, the system including an intravascular ultrasound for obtaining views of a blood vessel, a computer coupled to the intravascular ultrasound, a display coupled to the computer, a process residing in a memory coupled to the computer, the process comprising instructions to obtain a coronary tree segmentation to obtain a volume, split the volume into portions to obtain an adjacency graph for displaying on the display, compute a mean of a sub-volume of the sub-volume, obtain a gray value segmentation of the sub-volume, define a centerline of the blood vessel that avoids calcifications, detect an actual centerline of the blood vessel and enhancing lumen visualization of the blood vessel and display the inside of an artery as an intravascular ultrasound (IVUS) view with separation of the lumen of the blood vessel, the wall of the blood vessel and the calcified plaque.

Further disclosed herein is a computer-readable medium having computer executable instructions for performing a method including obtaining coronary tree segmentation to obtain a volume, splitting the volume into portions to obtain an adjacency graph, computing a mean of a sub-volume of the volume, obtaining gray value segmentation of the sub-volume, defining a centerline of a blood vessel that avoids calcifications and detecting actual centerline of the blood vessel and enhancing lumen visualization of the blood vessel.

TECHNICAL EFFECTS

The technical effect is the achievement of a display for inside of the coronary artery as an intravascular ultrasound (IVUS) view with separation of the lumen of the coronary, the wall of the vessel and the calcified plaque, and the automatic extraction of cardiac calcifications and obtaining of a better centerline in the tracking for display.

BRIEF DESCRIPTION OF THE DRAWINGS

The disclosure and embodiments thereof will become apparent from the following description and the appended drawings, in which the like elements are numbered alike.

DETAILED DESCRIPTION

Exemplary embodiments include systems and methods to detect cardiac calcifications. In exemplary implementations, high gray levels characterize the calcifications in the cardiac coronaries. Calcification detection systems and methods provide high gray level difference between the coronaries (contrast product) and the calcifications, and in the variability of the calcifications gray level. The detection systems and methods allow the improvement of the lumen visualization and stenosis analysis.

Further exemplary embodiments include systems and methods that provide a view that distinguishes lumen, wall of the vessel, calcification, plaque, etc. Therefore, IVUS visualization of the coronary is extended to CT cardiac images. As such, a volume rendering based IVUS views to display soft, calcified & mix plaque, lipid core, lumen and wall of vessel is provided. In exemplary implementations, separation of lumen, wall of the vessel, calcifications and soft plaque and display these components with different renderings in judicious views is provided. A graphical user interface (GUI) can further be provided that provides the views with the ability to manipulate and modify the views as desired. It is appreciated that IVUS is a catheter-based technique, which provides real-time high-resolution images allowing precise tomographic assessment of lumen area, wall of vessel, plaque size, and composition of a coronary. In exemplary embodiments, the coronary arteries are the most frequent imaging target. IVUS is used in the coronary arteries to determine the amount of disease at any particular point of the coronary artery. However, it is appreciated that the systems and methods described herein are further contemplated to target other blood vessels including but not limited to arteries, veins, etc.

Further exemplary embodiments allow segmenting the calcifications. In exemplary implementations, unique thresholds are defined for the various components of a given blood vessel. Furthermore, unique thresholds are defined for different aspects of calcifications. Therefore, a given unique threshold allows extracting the calcifications but can be different from an exam to another (from 1400 to 1600). Therefore, methods can automatically detect this threshold based on an initial 3D segmentation of the whole vessel tree or one coronary. In exemplary embodiments, manipulations of the thresholds, 3D segmentation renderings of a vessel tree, etc. can be provided via a user interface such as a GUI.

Figure 1:
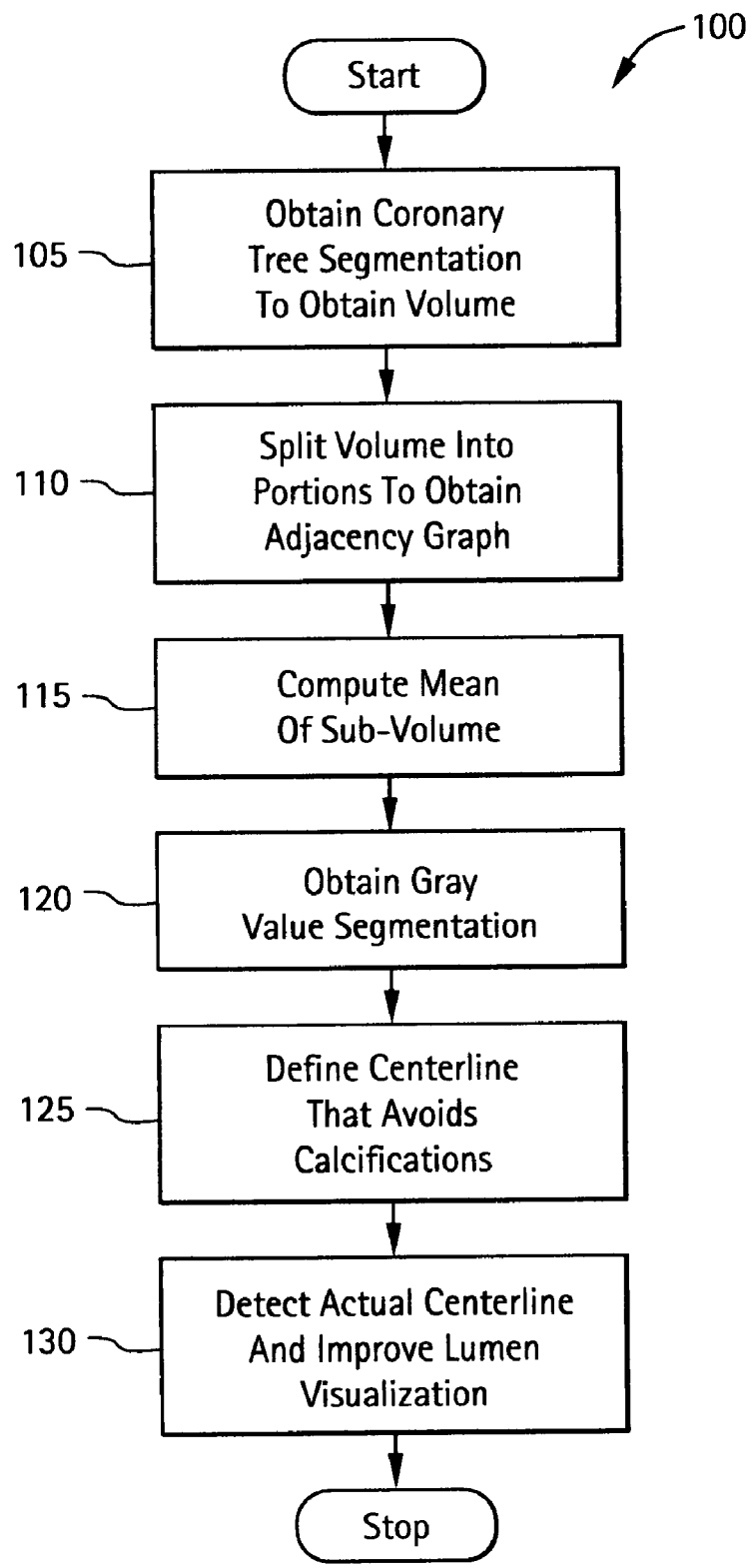
FIG. 1 illustrates an exemplary method for segmenting calcifications and separately extracting the lumen.
Figure 2:
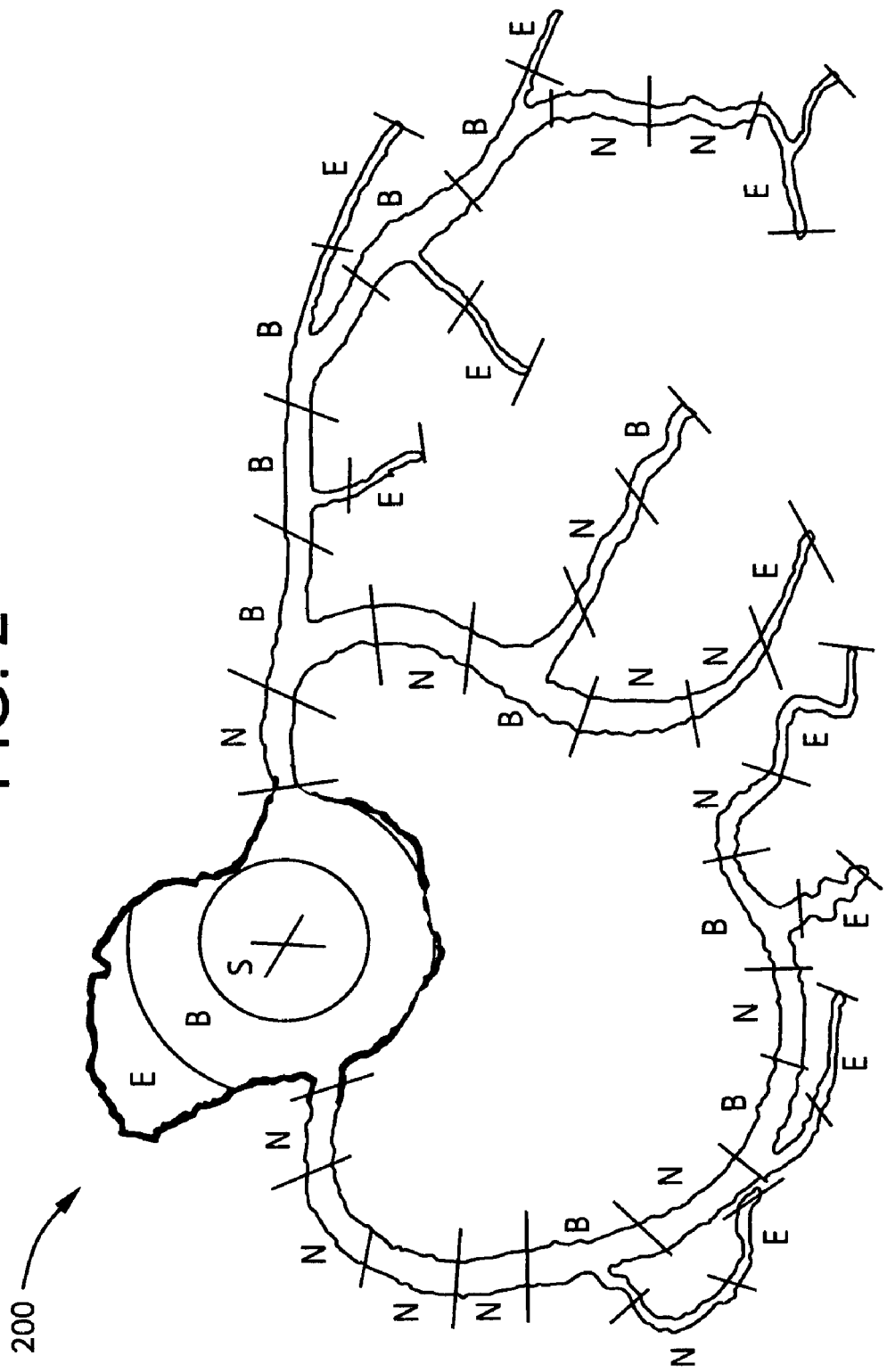
FIG. 2 illustrates an adjacency graph based on the distance map from aorta in accordance with exemplary embodiments.

FIG. 1 illustrates an exemplary method 100 for segmenting calcifications and extracting separately the lumen. At step 105, the coronary tree segmentation is obtained, using currently available automatic or semi automatic tools. In general, due to variations along a vessel obtaining a robust centerline that does not go into calcifications can implement explicit calcification segmentation to obtain the centerline. The coronary tree segmentation represents a volume that is split into several portions. As such, a volume rendering is obtained at step 105. At step 110, an adjacency graph is built. In an exemplary implementation, the adjacency graph built at step 110 is done based on distance maps. FIG. 2 illustrates an adjacency graph 200 based on the distance map from aorta in accordance with exemplary embodiments, with letter annotations regarding arterial segment type.

At step 115, the mean of sub-volume is computed. In an exemplary implementation, the maximum mean among all the mean values can be correlated with the ideal threshold that extracts the calcifications.

Figure 3:
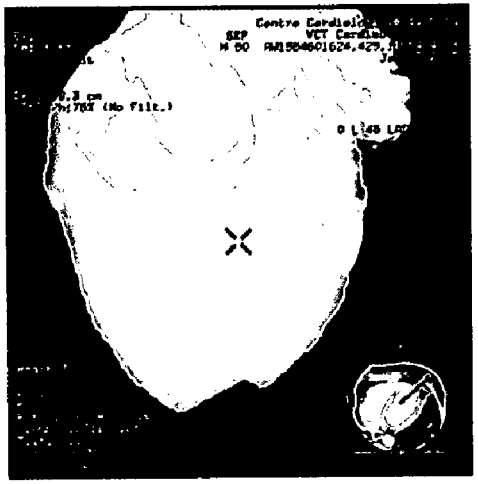
FIG. 3 illustrates several views of calcifications and stent detection in accordance with exemplary embodiments.
Figure 3:
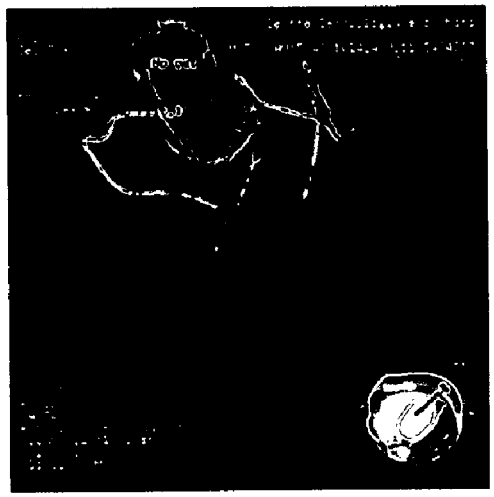
Figure 3:
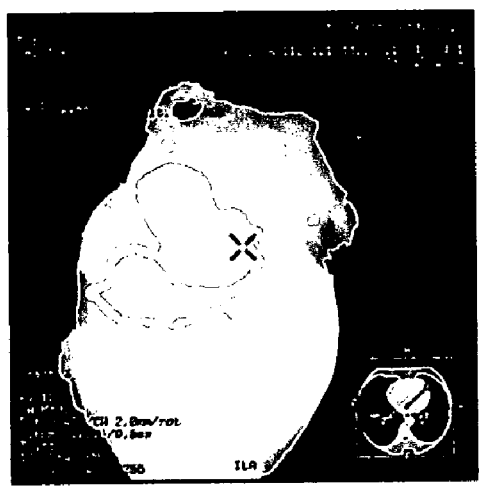
Figure 3:
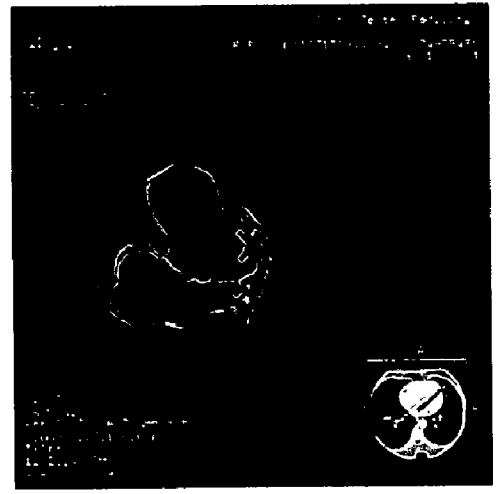
Figure 3:
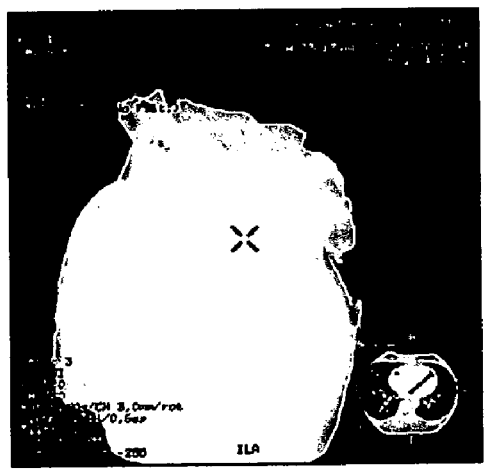
Figure 3:
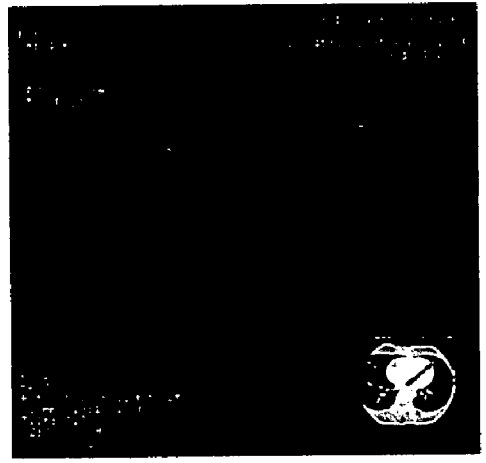

At step 120, the gray value segmentation of the calcifications is obtained. In an exemplary implementation, the calcifications in the coronary are the gray values higher than the maximum mean plus a constant value (e.g., 80). In another implementations, if the detected threshold is too low, that is, under a pre-determined threshold (e.g., 1300), there can be an indication that there is no calcification. FIG. 3 illustrates several views of calcifications and stent detection in accordance with exemplary embodiments.

Figure 4:
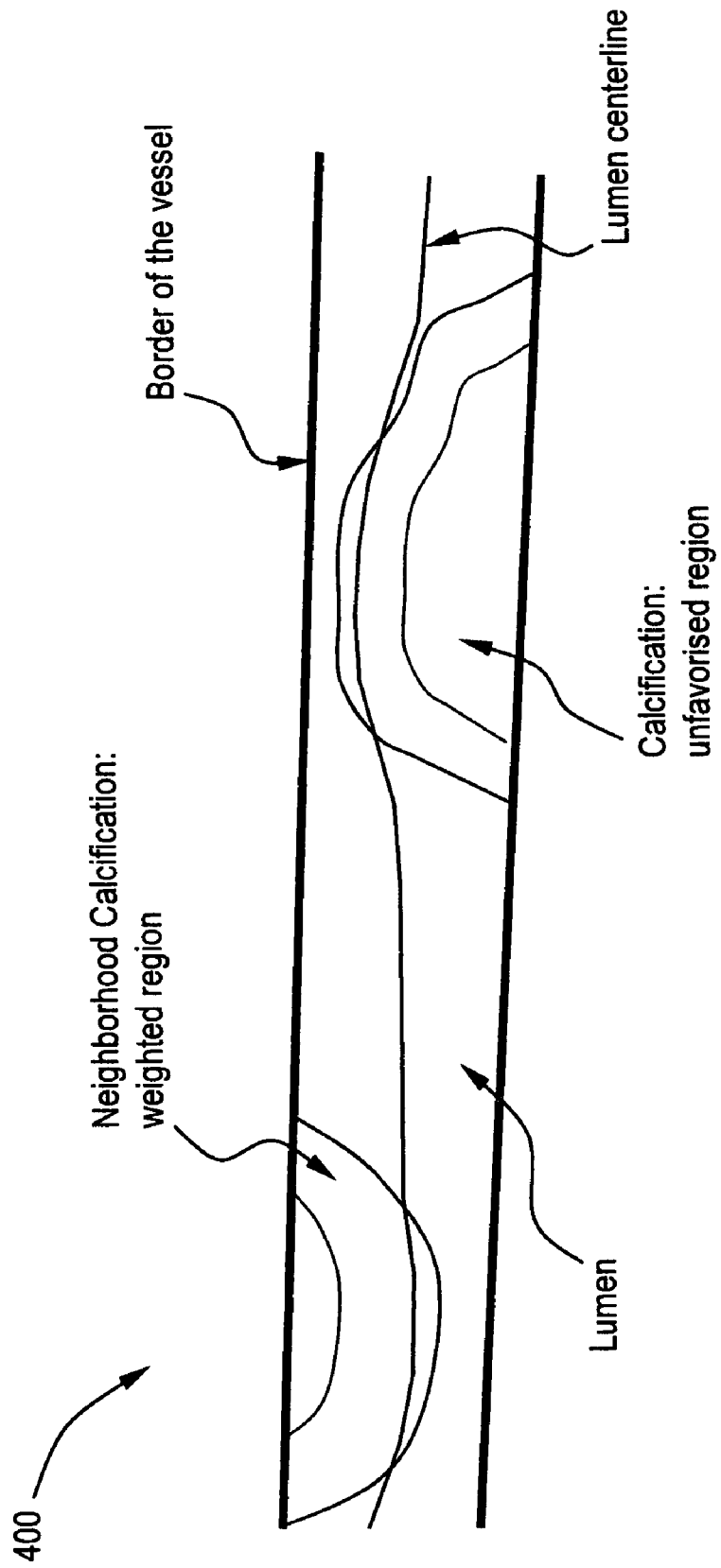
FIG. 4 illustrates a rendition of an artery in accordance with exemplary embodiments illustrating tracking improvement after calcifications detection.

At step 125, the automatic detection of the calcifications is used in tracking algorithms in accordance with exemplary embodiments to define a centerline that avoids the calcifications. In general, if there is no calcification, the tracking detects the most homogenous centerline. In exemplary implementations, privileged and unprivileged regions are defined around the calcifications. The regions guide the centerline out of the calcifications and in the center of the lumen. The calcifications are the unprivileged region and the neighborhood of the calcifications is privileged using weight in function of the distance from the border of the vessel. FIG. 4 illustrates a rendition 400 of an artery in accordance with exemplary embodiments illustrating tracking improvement after calcifications detection. It is therefore appreciated that the systems and methods described herein can be used to define and place a centerline both avoiding calcifications as well as placement in a homogeneous position within the blood vessel.

Figure 5:
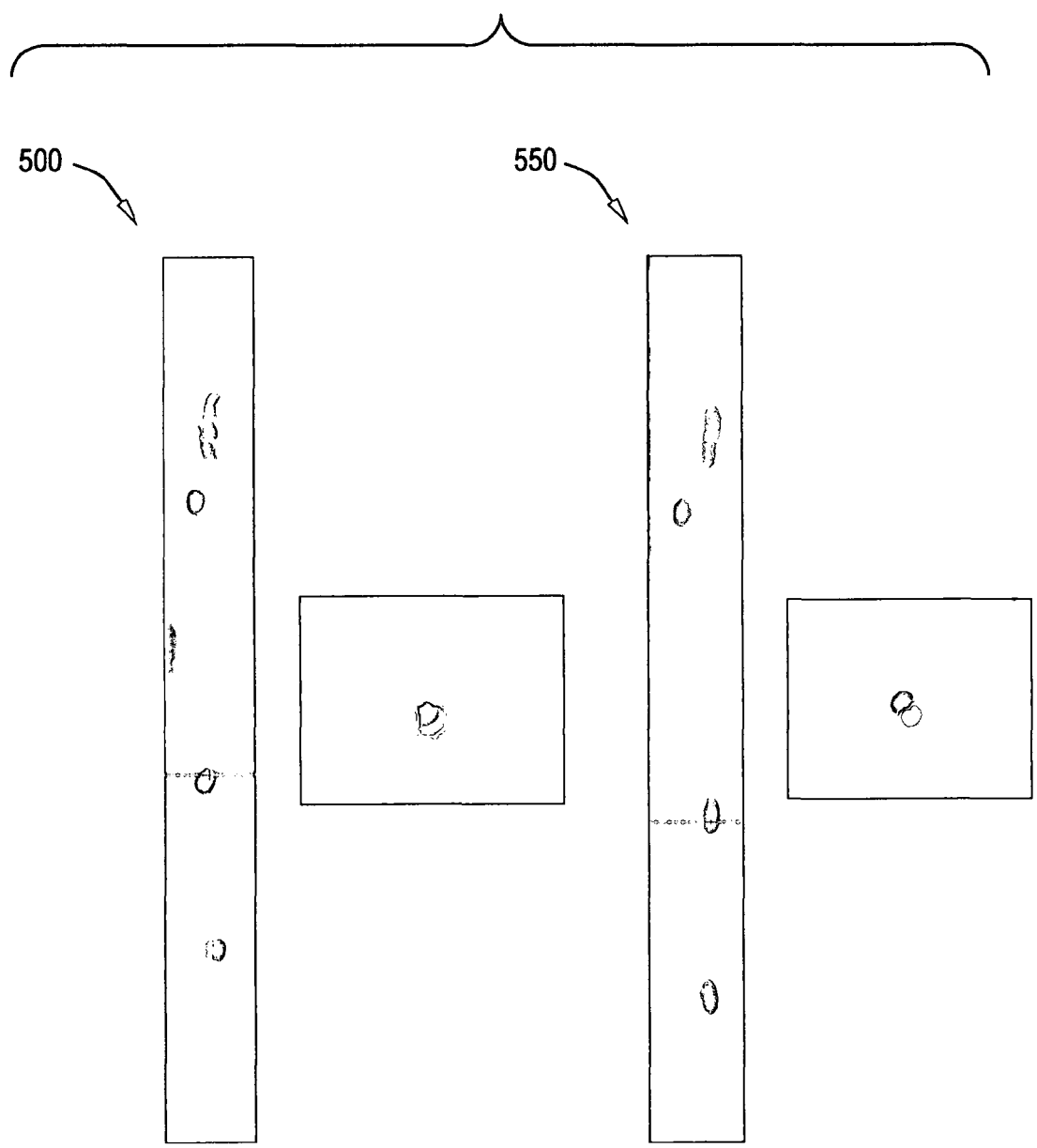
FIG. 5 illustrates an exemplary lumen views and cross sections.

Finally, at step 130 the actual centerline is detected and thus the lumen visualization is easily improved. The lumen volume improvement increases the reliability of the measurements and of the stenosis analysis. FIG. 5 illustrates an exemplary lumen views and cross sections 500, 550. View 500 illustrates no calcifications detected and view 550 illustrates detected calcifications.

As discussed above, the systems and methods described herein allow detecting the cardiac calcifications. The data and information obtained can be used in some other algorithms that further improve the quality the centerline. As such, cardiac calcifications and improved vessel centerline algorithms are obtained.

As further discussed above, exemplary embodiment include systems and methods for display of the inside of the coronary artery as an IVUS view with separation of the lumen of the coronary, the wall of the vessel and the calcified plaque. In exemplary implementations, separation of lumen, wall of the vessel, calcifications and soft plaque and display these components with different renderings in judicious views is provided. As further discussed above, due to variations along a vessel obtaining a robust IVUS can be obtained by explicit calcification segmentation to obtain the IVUS.

In accordance with exemplary embodiments, a threshold defines each component (e.g., lumen, wall, soft plaque, calcification, etc.). The automatic segmentation of the calcifications is used to define the object 'calcifications'. Furthermore, the detection of the cardiac calcifications by an adaptive threshold is defined in accordance with exemplary embodiments as described above.

Figure 6:
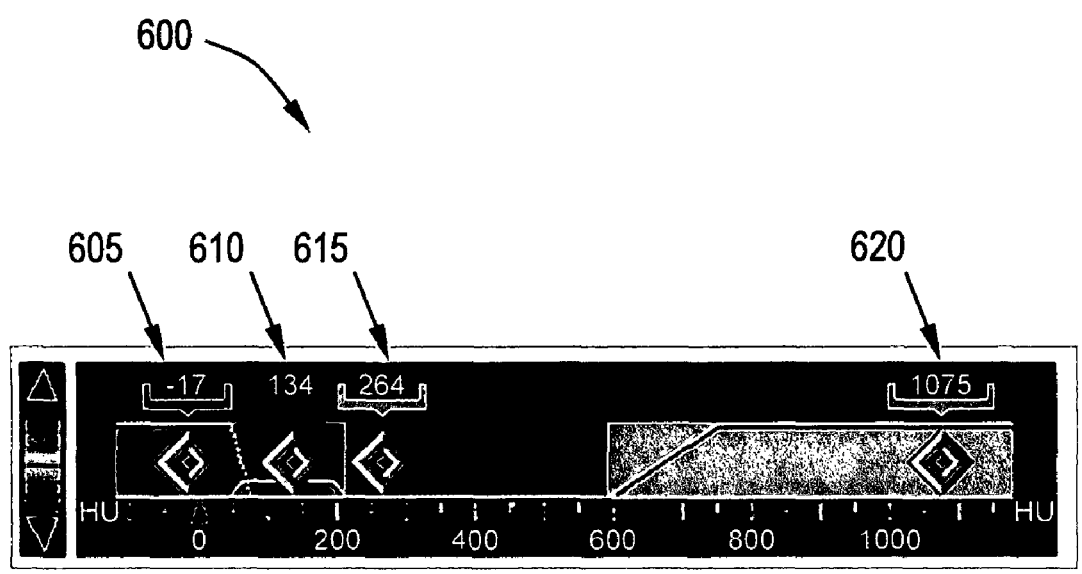
FIG. 6 illustrates an exemplary threshold scale as defines a view of lumen, wall of vessel, calcifications and plaque.

FIG. 6 illustrates an exemplary threshold scale as defines a view of lumen, wall of vessel, calcifications and plaque. For example, a first threshold 605 set at −17 can define the lumen of a blood vessel. Another threshold 610 set at 134 can define the wall of the vessel. Another threshold 615 set at 615 set at 264 can define calcifications of the vessel. Another threshold 620 set at 1075 can define plaques within the vessel. It is appreciated and understood that there are a variety of thresholds and associated colors that can be set to provide a visual representation of the vessel and accompanying calcifications on a user interface such as a GUI.

Figure 8:
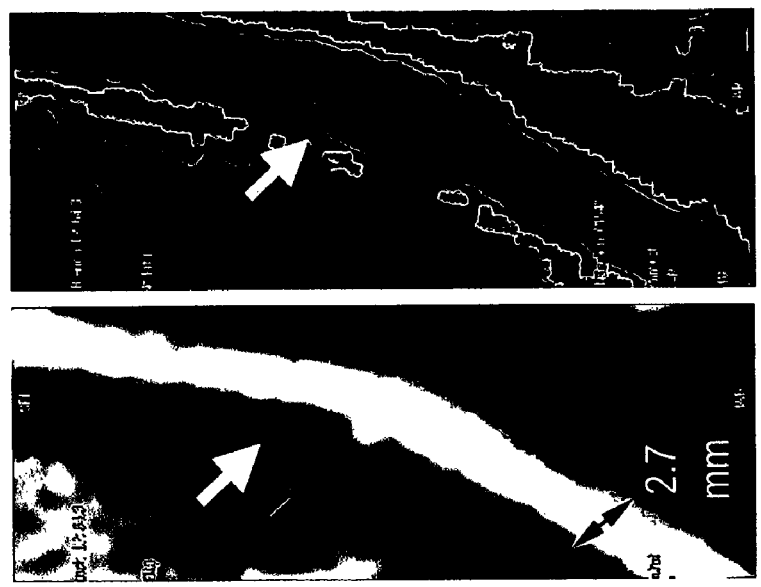
FIG. 8 illustrates an exemplary view of ulcerated plaque in accordance with exemplary embodiments.
Figure 7:
FIG. 7 illustrates an exemplary view of calcified plaque in accordance with exemplary embodiments.
Figure 10:
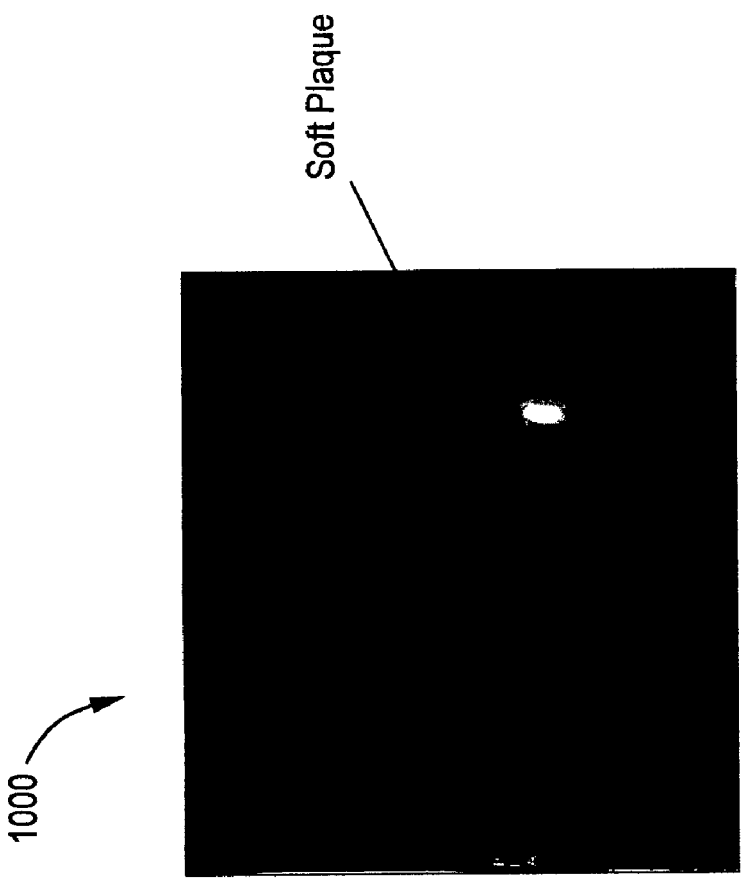
FIG. 10 illustrates an exemplary view of soft plaque in accordance with exemplary embodiments.
Figure 9:
FIG. 9 illustrates an exemplary view of calcifications in accordance with exemplary embodiments.

With the thresholds defined as discussed above with respect to FIG. 6, several visual representations are possible. FIG. 7 illustrates an exemplary view 700 of calcified plaque in accordance with exemplary embodiments. FIG. 8 illustrates an exemplary view 800 of ulcerated plaque in accordance with exemplary embodiments. FIG. 9 illustrates an exemplary view 900 of calcifications in accordance with exemplary embodiments. FIG. 10 illustrates an exemplary view 1000 of soft plaque in accordance with exemplary embodiments.

Figure 11:
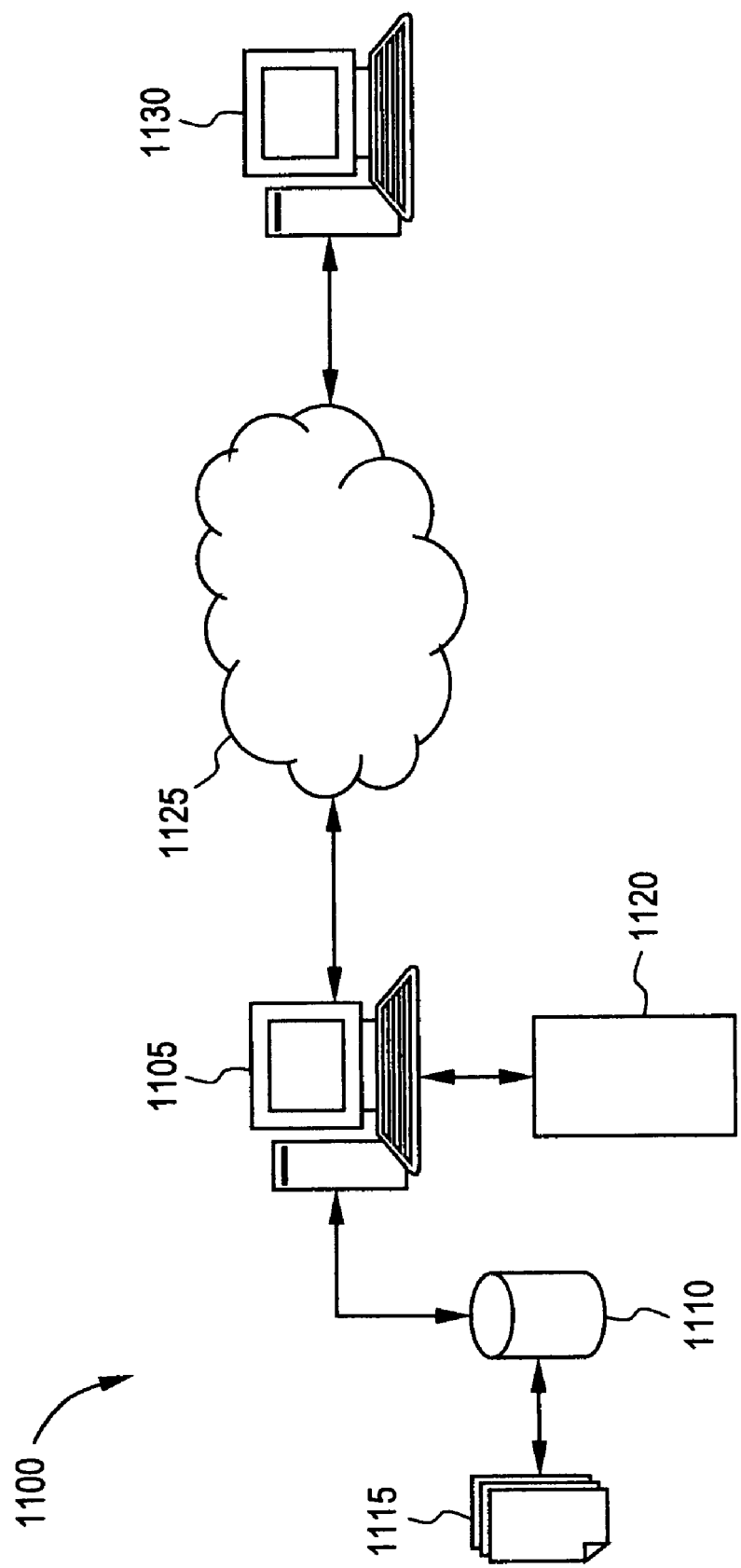
FIG. 11 illustrates system in which the methods and applications described herein may be implemented in accordance with exemplary embodiments.

FIG. 11 illustrates system 1100 in which the methods and applications described herein may be implemented in accordance with exemplary embodiments. System 1100 generally includes a general-purpose computer 1105 coupled to storage medium 1110 on which one or more applications 1115 can reside. Applications 1115 may implement any of the methods described herein. System 1100 can further include equipment 1120 on which data in accordance with exemplary embodiments can be measured and transferred to computer 1105. It is understood that computer 1105 can be a desktop, laptop, handheld, etc. It is further understood that equipment 1120 can include any suitable measurement and data acquisition equipment in accordance with exemplary embodiments. System 1100 can optionally be coupled to and in communication with network 1125, which can be coupled to an additional computer 1130, which can be in communication with general-purpose computer 1105.

The methods described herein can be implemented in software (e.g., firmware), hardware, or a combination thereof. For example, the methods can be implemented as an executable program, and is executed by a special or general-purpose digital computer, such as general-purpose computer 1105 described above or workstation, minicomputer, or mainframe computer, etc.

Generally, in terms of hardware architecture, as shown in FIG. 11, the general-purpose computer 1105 includes a processor, memory, and one or more input and/or output (I/O) devices (or peripherals) that are communicatively coupled via a local interface. The local interface can be, for example but not limited to, one or more buses or other wired or wireless connections, as is known in the art. The local interface may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor can be a hardware device for executing software, particularly that stored in memory. The processor can be any custom made or commercially available processor, a central processing unit (CPU), an auxiliary processor among several processors associated with the general-purpose computer 1105, a semiconductor based microprocessor (in the form of a microchip or chip set), a macroprocessor, or generally any device for executing software instructions.

The memory can include any one or combination of volatile memory elements (e.g., random access memory (RAM), such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory may incorporate electronic, magnetic, optical, and/or other types of storage media. Note that the memory can have a distributed architecture, where various components are situated remote from one another, but can be accessed by the processor.

The software in memory may include one or more separate programs, each of which comprises an ordered listing of executable instructions for implementing logical functions. In the example of FIG. 11, the software in the memory includes the methods in accordance with exemplary embodiments and a suitable operating system (O/S). The operating system essentially controls the execution of other computer programs, such as the methods described herein, and provides scheduling, input-output control, file and data management, memory management, and communication control and related services.

The methods described herein can be implemented as a source program, executable program (object code), script, or any other entity comprising a set of instructions to be performed. When a source program, then the program needs to be translated via a compiler, assembler, interpreter, or the like, which may or may not be included within the memory 14, so as to operate properly in connection with the O/S 22. Furthermore, the methods described herein can be written as (a) an object oriented programming language, which has classes of data and methods, or (b) a procedure programming language, which has routines, subroutines, and/or functions, for example but not limited to, C, C++, Pascal, Basic, Fortran, Cobol, Perl, Java, and Ada, etc.

The I/O devices may include input devices, for example but not limited to, a keyboard, mouse, scanner, microphone, etc. Furthermore, the I/O devices may also include output devices, for example but not limited to, a printer, display, etc. Finally, the I/O devices may further include devices that communicate both inputs and outputs, for instance but not limited to, a NIC or modulator/demodulator (for accessing other files, devices, systems, or a network), a radio frequency (RF) or other transceiver, a telephonic interface, a bridge, a router, etc.

If the general-purpose computer 1105 is a PC, workstation, intelligent device or the like, the software in the memory may further include a basic input output system (BIOS) (omitted for simplicity). The BIOS is a set of essential software routines that initialize and test hardware at startup, start the O/S, and support the transfer of data among the hardware devices. The BIOS is stored in ROM so that the BIOS can be executed when the general-purpose computer 1105 is activated.

When the general-purpose computer 1105 is in operation, the processor is configured to execute software stored within the memory, to communicate data to and from the memory, and to generally control operations of the computer pursuant to the software. The methods described herein and the O/S, in whole or in part, but typically the latter, are read by the processor, perhaps buffered within the processor, and then executed.

When the methods are implemented in software, as is shown in FIG. 11, the methods can be stored on any computer readable medium for use by or in connection with any computer related system or method. In the context of this document, a computer readable medium is an electronic, magnetic, optical, or other physical device or means that can include or store a computer program for use by or in connection with a computer related system or method.

The methods described herein can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In an alternative embodiment, where the methods are implemented in hardware, the methods can implemented with any or a combination of the following technologies, which are each well known in the art: a discrete logic circuit (s) having logic gates for implementing logic functions upon data signals, an application specific integrated circuit (ASIC) having appropriate combinational logic gates, a programmable gate array(s) (PGA), a field programmable gate array (FPGA), etc.

As described above, the exemplary embodiments can be in the form of computer-implemented processes and apparatuses for practicing those processes. The exemplary embodiments can also be in the form of computer program code including instructions embodied in tangible media, such as floppy diskettes, CD ROMs, hard drives, or any other computer-readable storage medium, wherein, when the computer program code is loaded into and executed by a computer, the computer becomes an apparatus for practicing the exemplary embodiments. The exemplary embodiments can also be in the form of computer program code, for example, whether stored in a storage medium, loaded into and/or executed by a computer, or transmitted over some transmission medium, loaded into and/or executed by a computer, or transmitted over some transmission medium, such as over electrical wiring or cabling, through fiber optics, or via electromagnetic radiation, wherein, when the computer program code is loaded into an executed by a computer, the computer becomes an apparatus for practicing the exemplary embodiments. When implemented on a general-purpose microprocessor, the computer program code segments configure the microprocessor to create specific logic circuits.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of cardiac diagnostics, the method comprising:
    obtaining in a processor coronary tree segmentation from intravascular ultrasound (IVUS) views to obtain cardiac volume information;
    splitting in a processor the volume into portions to obtain an adjacency graph for display on a graphical user interface;
    computing in a processor a mean of a sub-volume of the volume to obtain a mean threshold above which indicates that calcifications are present;
    obtaining in a processor gray value segmentation of the sub-volume, the gray value segmentations each having a value related to the mean of the sub-volume, including the threshold above which indicates that the calcifications are present;
    defining in a processor a centerline of a blood vessel that avoids calcifications within the blood vessel; and
    detecting in a processor an actual centerline of the blood vessel and enhancing lumen visualization of the blood vessel for display on the graphical user interface.

2. The method as claimed in claim 1 further comprising displaying the inside of an artery as an (IVUS) view on the graphical user interface.

3. The method as claimed in claim 2 wherein the view comprises a visual separation of the lumen of the coronary, the wall of the coronary and the calcified plaque.

4. A method for extracting and tracking cardiac calcification image volumes in a blood vessel, the method comprising:
    obtaining in a processor intravascular ultrasound (IVUS) views of the blood vessel for display on a graphical user interface;
    defining in a processor a blood vessel tree segmentation of the IVUS views;
    extracting in a processor an image volume of cardiac calcifications from the tree segmentation; and
    splitting in a processor the volume into portions to obtain an adjacency graph for display on the graphical user interface.

5. The method as claimed in claim 4 further comprising defining a sub-volume from the volume.

6. The method as claimed in claim 5 further comprising computing a mean of the sub-volume.

7. The method as claimed in claim 4 further comprising obtaining gray value segmentations to differentiate the blood vessel from the calcifications.

8. The method as claimed in claim 4 further comprising defining a centerline of the blood vessel.

9. The method as claimed in claim 8 wherein the centerline excludes calcifications in the blood vessel.

10. The method as claimed in claim 9 wherein the centerline excludes calcifications in the blood vessel by defining privileged and un-privileged regions around the calcifications.

11. The method as claimed in claim 10 further comprising computing an actual centerline, thereby having enhanced lumen visualization.

12. The method as claimed in claim 4 further comprising displaying the inside of an artery as an IVUS view with separation of the blood vessel components for display on the graphical user interface.

13. The method as claimed in claim 12 wherein the blood vessel components include at least one of the lumen of the blood vessel, the wall of the blood vessel, and the calcified plaque.

14. The method as claimed in claim 13 wherein the blood vessel in the coronary artery.

15. A method for extracting and tracking cardiac calcification image volumes in a blood vessel, the method comprising:
    obtaining in a processor intravascular ultrasound (IVUS) views of the blood vessel for display on a graphical user interface;
    defining in a processor a blood vessel tree segmentation of the IVUS views; and
    extracting in a processor an image volume of cardiac calcifications from the tree segmentation;
    defining in a processor a sub-volume from the volume; and
    computing in a processor a mean of the sub-volume.

16. The method as claimed in claim 15 splitting the volume into portions to obtain an adjacency graph for display on the graphical user interface.

17. The method as claimed in claim 15 further comprising obtaining gray value segmentations to differentiate the blood vessel from the calcifications.

18. The method as claimed in claim 15 further comprising defining a centerline of the blood vessel.

19. The method as claimed in claim 18 wherein the centerline excludes calcifications in the blood vessel.

20. The method as claimed in claim 19 wherein the centerline excludes calcifications in the blood vessel by defining privileged and un-privileged regions around the calcifications.

21. The method as claimed in claim 20 further comprising computing an actual centerline, thereby having enhanced lumen visualization.

22. The method as claimed in claim 15 further comprising displaying the inside of an artery as an IVUS view with separation of the blood vessel components for display on the graphical user interface.

23. The method as claimed in claim 22 wherein the blood vessel components include at least one of the lumen of the blood vessel, the wall of the blood vessel, and the calcified plaque.

24. The method as claimed in claim 23 wherein the blood vessel in the coronary artery.

25. A method for extracting and tracking cardiac calcification image volumes in a blood vessel, the method comprising:
obtaining intravascular ultrasound (IVUS) views of the blood vessel for display on a graphical user interface;
defining a blood vessel tree segmentation of the IVUS views;
extracting an image volume of cardiac calcifications from the tree segmentation; and
defining a centerline of the blood vessel,
wherein the centerline excludes calcifications in the blood vessel,
wherein the centerline excludes calcifications in the blood vessel by defining privileged and un-privileged regions around the calcifications.

26. The method as claimed in claim 25 further comprising computing an actual centerline, thereby having enhanced lumen visualization.

27. A system for extracting and tracking cardiac calcifications in a blood vessel, the system comprising:
an intravascular ultrasound device for obtaining views of a blood vessel;
a computer coupled to the intravascular ultrasound device;
a display coupled to the computer;
a process residing in a memory coupled to the computer, the process comprising instructions to:
obtain a coronary tree segmentation from intravascular ultrasound (IVUS) views to obtain a volume;
split the volume into portions to obtain an adjacency graph for displaying on the display;
compute a mean of a sub-volume of the sub-volume to obtain a mean threshold above which indicates that calcifications are present;
obtain a gray value segmentation of the sub-volume, the gray value segmentations each having a value related to the mean of the sub-volume, including the threshold above which indicates that the calcifications are present;
define a centerline of the blood vessel that avoids calcifications;
detect an actual centerline of the blood vessel and enhancing lumen visualization of the blood vessel; and
display the inside of an artery as an intravascular ultrasound (IVUS) view with separation of the lumen of the blood vessel, the wall of the blood vessel and the calcified plaque.

28. A non-transitory computer-readable medium having computer executable instructions for performing a method comprising:
obtaining coronary tree segmentation from intravascular ultrasound (IVUS) views to obtain a volume;
splitting the volume into portions to obtain an adjacency graph;
computing a mean of a sub-volume of the volume to obtain a mean threshold above which indicates that calcifications are present;
obtaining gray value segmentation of the sub-volume, the gray value segmentations each having a value related to the mean of the sub-volume, including the threshold above which indicates that the calcifications are present;
defining a centerline of a blood vessel that avoids calcifications; and
detecting actual centerline of the blood vessel and enhancing lumen visualization of the blood vessel.

* * * * *